United States Patent [19]

Auer et al.

[11] Patent Number: 5,789,628
[45] Date of Patent: Aug. 4, 1998

[54] PRODUCTION OF 2,2'-BIS (4-HYDROXYPHENYL) PROPANES IN THE PRESENCE OF ORGANOPOLYSILOXANES CONTAINING SULPHONATE AND MERCAPTO GROUPS

[75] Inventors: Emmanuel Auer, Frankfurt; Stefan Wieland, Offenbach; Hans Lansink-Rotgerink, Glattbach; Hauke Jacobsen, Bruchkoebel; Heike Riedemann, Moembris, all of Germany

[73] Assignee: Degussa Aktiengesellschaft, Frankfurt am Main, Germany

[21] Appl. No.: 710,756

[22] Filed: Sep. 20, 1996

[30] Foreign Application Priority Data

Sep. 29, 1995 [DE] Germany .................. 195 36 366.3

[51] Int. Cl.$^6$ ........................................ C07C 39/12
[52] U.S. Cl. ................................. 568/727; 528/30
[58] Field of Search .................... 568/727; 528/30

[56] References Cited

U.S. PATENT DOCUMENTS 5,075,511  12/1991  Li .................................... 568/727

FOREIGN PATENT DOCUMENTS 0693470  1/1996  European Pat. Off. .

2685221  6/1993  France .

*Primary Examiner*—Gary Geist
*Assistant Examiner*—Sreeni Padmanabhan
*Attorney, Agent, or Firm*—Beveridge, DeGrandi, Weilacher & Young, L.L.P.

[57] ABSTRACT

A process for the production of 2,2'-bis(4-hydroxyphenyl) propanes by reacting the corresponding phenols and carbonyl compounds in the presence of organopolysiloxanes containing sulphonate and mercapto groups and acting as a catalyst, consisting of units of the formula $$[O_{3/2}—Si—R^1—SO_3—]_xM^{x+} \qquad (I),$$

wherein $R^1$ is a linear or branched alkylene group having 1 to 12 C atoms, a cycloalkylene group having 5 to 8 C atoms or a unit of the formulae

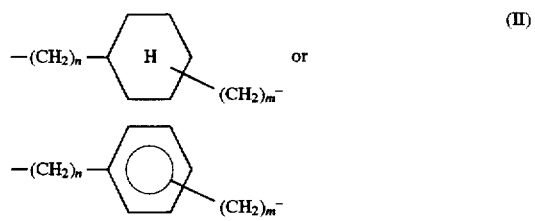

and units of the formula $$O_{3/2}—Si—R^2—SH \qquad (III)$$

5 Claims, No Drawings

PRODUCTION OF 2,2'-BIS (4-HYDROXYPHENYL) PROPANES IN THE PRESENCE OF ORGANOPOLYSILOXANES CONTAINING SULPHONATE AND MERCAPTO GROUPS

INTRODUCTION AND BACKGROUND

The present invention relates to the method for the production of 2,2'-bis(4-hydroxyphenyl)propanes by the reaction of corresponding phenols with ketones in the presence of organopolysiloxanes containing sulphonate and mercapto groups. The reaction equation for the synthesis of bisphenol A (BPA) is stated by way of example:

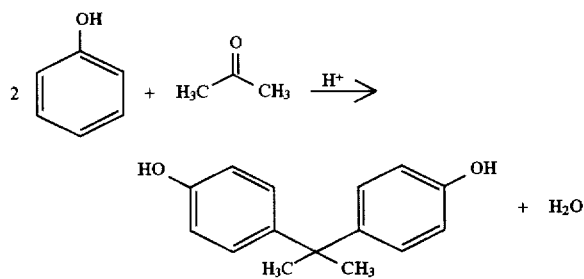

The homogeneously HCl-catalyzed process used heretofore has today largely been replaced by a process with organic ion exchangers based on styrene/divinylbenzene. The heterogeneously catalyzed process is performed industrially without solvent in a melt at a temperature of 40°–120° C., wherein phenol and acetone are generally used in a ratio of 10:1 to 15:1. Since very highly pure bisphenol A is required for further processing into plastics and approximately half the production costs arise from purification of the product, attempts have been made to perform the reaction as selectively as possible at elevated acetone conversion rates.

In order to increase the activity and selectivity of the heterogeneous catalysts, bifunctional aminomercaptan compounds (for example thiazolines, mercaptoalkylamines) are used as co-catalysts, which are attached to the sulphonic acid residue of the organic ion exchanger via the amine group (DE-OS 37 27 641, U.S. Pat. No. 3,634,341). Before the beginning of the reaction, the acidic ion exchangers must first be pretreated in phenol and then modified with the compounds containing sulphur. All possible degrees of modification of ion exchangers have been patented, but preferably 5–30 mol. % of the exchange capacity of the resin is modified by mercapto compounds (EP-A1-0 620 041).

Bisphenol A is generally produced in a continuous process, in which, after the reaction, the bisphenol A crystallizes out with phenol as a 1:1 adduct. Phenol is removed in various washing processes with water and organic solvents and recrystallized as the pure product. At residence times of up to 6 h on the catalyst, bisphenol A yields are between 90 and 95% relative to the minority component acetone at selectivities of 95%. The principal by-product is 2,4'-dihydroxyphenylpropane (o,p-bisphenol A). Further compounds occurring only in very small quantities, such as 4-hydroxyphenyl-2,2,4-trimethylchroman or triphenols, are responsible for the yellow color and are also undesirable.

However, the catalytic activity and selectivity of the modified organic ion exchangers decreases after only a relatively short time. One cause is the cleavage of the mercapto compounds from the surface of the sulphonic acid ion exchangers (deactivation of the co-catalytic unit), which is mentioned in various patents (EP-A-0 583 712, EP-A1-0 620 041). The loss in reactivity of the modified ion exchange resins may be partially reversed in catalysts having a low alkyl-SH content by regeneration (EP-A1 0 620 041). All in all, however, the modified ion exchangers have service lives up to 10 times shorter than unmodified systems, so entailing regeneration measures, resulting in inadequate space/time yields and, ultimately, being uneconomic. Regenerating, for example, large quantities of Lewatit is time consuming, costly and an equally large quantity of fresh ion exchanger must be available in order to maintain BPA production (c.f. DE 43 12 039). Moreover, it is clear from the stated patents that more frequent remodification of the organic ion exchangers with promoters containing SH makes no economic sense, as the regeneration operations never achieve the initial activity of the ion exchanger, but instead continuously decreasing activity is observed (DE-A1 43 12 038). Furthermore, hydraulic problems occur in the continuous process with slightly crosslinked polystyrene/divinylbenzene ion exchangers due to the elevated compressibility of such resins and the associated pressure loss, channelling in the fixed bed, reduction in throughput and reduced acetone conversion.

U.S. Pat. No. 5,315,042 discloses another process for the production of BPA. Known cation exchangers are used as the catalyst, wherein mercapto compounds are obviously added to the reaction mixture as promoters. At a WHSV of 1.0, acetone conversion of 81% is established.

SUMMARY OF THE INVENTION

It has now been found that mercapto groups are not lost from the novel catalyst used according to the invention, so no decrease in activity and selectivity is observed.

The present invention provides a process for the production of 2,2'-bis(4-hydroxyphenyl)propanes by reacting the corresponding phenols and carbonyl compounds in the presence of an acidic catalyst. The process is carried out by performing the reaction at a temperature of between 40° and 150° C. in the presence of a shaped organopolysiloxane containing sulphonate and mercapto groups, consisting of units of the formula $$[O_{3/2}—Si—R^1—SO_3—]_xM^{x+} \qquad (I),$$

wherein $R^1$ is a linear or branched alkylene group having 1 to 12 C atoms, a cycloalkylene group having 5 to 8 C atoms or a unit of the general formulae

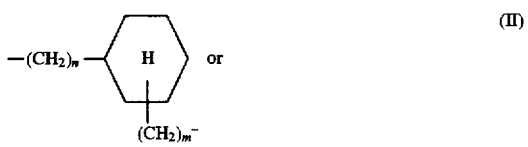

in which n or m is a number from 0 to 6 and states the number of methylene groups connected in the silicon or sulphur position, M equals $H^+$ or optionally also $NH_4^+$ or a conventional metal ion, such as for example an alkali metal or alkaline earth metal ion, having a valency of x equals 1 to 4, wherein $H^+$ is preferably always present, even if only at the slightest concentration, in a quantity of greater than 1% of the ion exchange capacity of (I), and units of the formula $$O_{3/2}\text{—Si—}R^2\text{—SH} \qquad (III)$$

where $R^2=R^1$, wherein the free valencies of the oxygen atoms attached to the silicon atoms are saturated by the silicon atoms of further groups of the formulae (I) and/or (II) and/or by the metal atom oxygen groups of the crosslinking linking members of the formulae $$SiO_{4/2} \qquad (IV)$$

optionally $R"SiO_{3/2}$, $R'SiO_{3/2}$, $R'_2SiO_{2/2}$ and optionally $AlO_{3/2}$, $R'AlO_{2/2}$ and/or $TiO_{4/2}$, $R"TiO_{3/2}$, $R'_2TiO_{2/2}$ $\qquad$ (V)

wherein R' is a methyl or ethyl group, and R" means phenyl or a linear or branched $C_2$—$C_{12}$ alkyl group.

The ratio of groups of the formula (I) to groups of the formula (III) ranges from 10:1 to 1:10.

The ratio of groups of the formula (I) to groups of the formula $SiO_{4/2}$ ranges from 1:3 to 1:20 and the ratio of groups of the formula $SiO_{4/2}$ to groups of the formula (V) ranges from 1:0 to 1:0.5. After the reaction the desired 2,2'(4-hydroxyphenyl) propane product is separated.

$R^1$ and $R^2$ in the formulae (I) and (III) above preferably have the same meaning, wherein $R^1$ and $R^2$ in particular represent the propylene residue and $M^{x+}$ represents $H^+$.

DETAILED DESCRIPTION OF INVENTION

Depending upon their pre-treatment, the spherically shaped polysiloxanes used in the process of this invention have a particle diameter of 0.01 to 3.0, preferably of 0.05 to 2.0 mm, a specific surface area of >0 to 1000 m²/g, preferably of >0 to 700 m²/g and a bulk density of 50 to 1000 g/l, preferably of 100 to 800 g/l. Pore diameter may be adjusted within the range from <0 to above 1000 mm.

These polysiloxanes are produced using the process described in DE 195 36 363, (relied on and incorporated herein by reference) in which sulphonated organosilicon compounds of the formula $$[(OH)_3Si\text{—}R^1\text{—}SO_3^-]_xM^{x+} \qquad (VI),$$

in which $R^1$, M and x have the same meanings as in the formula (I) and compounds which, on aqueous hydrolysis, form $SiO_{4/2}$ units, are mixed in a molar ratio of 1:3 to 1:20 in an aqueous alcoholic medium at 30° to 100° C. and are allowed to condense together.

The reaction to form the polysiloxanes proceeds at standard pressure or a pressure corresponding to the sum of partial pressures of the components present at the temperatures used. At the beginning, during or after the condensation reaction, but before curing, an organosilicon compound containing mercapto groups and of the formula $$(RO)_3Si\text{—}R^2\text{—}SH \qquad (VII)$$

is added to this mixture in a molar ratio to the compound according to the formula (VI) of 1:10 to 10:1 and optionally further compounds which form groups of the formula (V).

The alkoxy residue of compounds of the formula (VII) preferably corresponds to the alcohol used. The reaction mixture is adjusted to a temperature from room temperature to 120° C., preferably of 40° to 80° C., wherein viscosity increases and a viscous gel is formed. Within a period of time ranging from immediately after all the reaction components have been combined up to a maximum of 10 h after the beginning of the reaction, but preferably at the time of gelation, the siloxane solution is dispersed in a solvent immiscible with the siloxane solution.

The shaping phase involving conversion of the coherent, gel-like mass infiltrated with liquid into separate spherical particles begins when the (partially) gelled reaction mixture is combined with this solvent in the intended quantity.

The spherically shaped moist solid may be separated from the liquid dispersant using conventional methods, such as decanting, filtration or centrifugation.

After washing once more in an aqueous solution (which optionally contains HCl), the solid is optionally hydrothermally post-treated with stirring at a temperature of 90° to 170° C. for the purpose of post-curing.

Catalysts of the following type are preferably used:

9 $SiO_2 \cdot SiO_{3/2}(CH_2)_3SO_3H \cdot 2 SiO_{3/2}(CH_2)_3SH716$

10 $SiO_2 \cdot SiO_{3/2}(CH_2)_3SO_3H \cdot 3 SiO_{3/2}(CH_2)_3SH716$

10 $SiO_2 \cdot 2 AlO_{3/2} \cdot SiO_{3/2}CH_2\text{—}C_6H_4\text{—}CH_2SO_3H \cdot 2SiO_{3/2}(CH_2)_3SH$ 36 $SiO_2 \cdot 4 SiO_{3/2}(CH_2)_3SO_3H \cdot SiO_{3/2}(CH_2)_3SH$ 9 $SiO_2 \cdot SiO_{3/2}(CH_2)_3SO_3H \cdot 3 SiO_{3/2}(CH_2)_3SH \cdot SiO_{3/2}(CH_2)_3CH_3$ 6 $SiO_2 \cdot SiO_{3/2}(CH_2)_3SO_3H \cdot 2 SiO_{3/2}(CH_2)_3SH$ The present invention also provides a process for producing 2,2'-bis(4-hydroxyphenyl)propane of the formula:

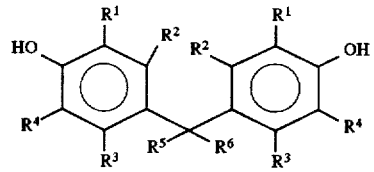

from phenols of the formula:

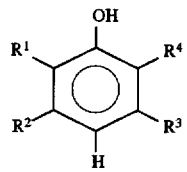

in which $R_1$, $R_2$, $R_3$ and $R_4$ mutually independently denote hydrogen, $C^1$ to $C^4$ alkyl groups, aromatic substituents or halogens, such as F, Cl, Br and I, preferably 2-methylphenol (o-cresol) 2, 6-dimethylphenol, 2-ethylphenol, 1,3,5-trimethylphenol (1,3,5-xylenol), 2,3,5,6-tetramethylphenol, 2-phenylphenol, 2-chlorophenol, 3-chlorophenol, 2-bromophenol, 2,6-dichlorophenol, in particular phenol. The reaction of the phenol of formula IX taken place with carbonyl compounds of the formula:

in which $R^5$ and $R^6$ mutually independently mean hydrogen, $C_1$ to $C_6$ alkyl, $C_6$ to $C_{10}$ cycloalkyl, $C_3$ to $C_{14}$ aryl, $C_7$ to $C_{20}$ arylalkyl, $C_7$ to $C_{20}$ alkylaryl or $R^5$ and $R^6$ form a saturated ring having 5 to 6 carbon atoms or heteroatoms. In particular, the following aldehydes and ketones are very suitable: formaldehyde, methyl ethyl ketone, methyl propyl ketone, diethyl ketone, cyclohexanone, and acetophenone. Acetone is preferably used.

The condensation of phenol derivatives according to the formula (IX) with carbonyl compounds according to the formula (X) may be performed continuously (fixed bed reactor) or discontinuously (slurry reactor) under the following conditions.

In discontinuous operation, 50 to 250 g, preferably 100 to 150 g dry weight of the polysiloxane used as catalyst according to the invention are generally used per molar equivalent of carbonyl compound used. The molar ratio of the starting compounds phenol (I) and acetone (II) ranges from 3:1 to 25:1, preferably from 5:1 to 15:1. Reaction temperatures are within the range from 40° to 150° C., preferably above the melting or solidification temperature of the components involved. Reaction times generally range between 10 minutes and 24 hours, preferably between 30 minutes and 6 hours.

In the continuous process, a mixture of phenols according to the formula (VII) and carbonyl compounds according to the formula (VIII) is generally passed through a fixed bed reactor in a ratio of 3:1 to 25:1, preferably from 5:1 to 15:1, 90% of the volume of the fixed bed reactor being filled with the polysiloxane to be used according to the invention. The temperature in the reactor is between 40° and 150° C., preferably between 60° and 75° C. The WHSV (weight hourly space velocity) ranges from 0.25 to 24 $h^{-1}$, preferably between 0.5 and 2 $h^{-1}$. The reaction mixture may flow through the reactor from the top downwards and from the bottom upwards.

The product mixture is then sent for recovery and purification, which are performed by conventional methods such as distillation and crystallization (as with the product stream from the discontinuously operated slurry reactor). Thus, for example, the resultant bisphenol in the reaction mixture may be cooled until crystallization begins and the phenol is removed by distillation or extraction from the mixed bisphenol/phenol crystals obtained by filtration. The bisphenol produced using this process may be used for known applications without further purification.

The advantages of the organofunctional polysiloxane catalysts (OPF) used according to the invention in comparison with the prior art are summarized below:

In comparison with catalysts based on Lewatit® and Amberlyst® and produced in accordance with prior art descriptions and with other prior art (c. f. U.S. Pat. No. 5,315,042), OFP catalysts have higher acetone conversion rates in the continuous process at comparable WHSV values.

Selectivities behave similarly: in the continuous process, the p/p-bisphenol A selectivity values are greater than 95.5% relative to reacted phenol.

When OFP catalysts are used, the quantity of nonisomerizable by-products is below 0.05% (c. f. EP 0 583 712 A2, selectivity for non-isomerizable by-products of 0.12% to 0.27%).

Selectivities for p/p-bisphenol A and the isomerizable products o/p-bisphenol A in the continuous process (WHSV=0.5 $h^{-1}$) are 99.95% and above, relative to reacted phenol.

At reaction temperatures of 100° C., pip-bisphenol A yields of 97% with quantitative conversion of acetone are achieved in discontinuous operation after 4 hours' reaction time.

Due to the covalent bonding of the co-catalytically active mercapto units onto the surface of the organofunctional polysiloxane matrix, such catalysts have elevated resistance to deactivation, which, in the prior art, occurs by leaching of the co-catalyst.

Moreover, covalent attachment of the SH groups neither requires additional modification with co-catalysts before the beginning of the reaction, nor the optional addition of the co-catalyst in homogeneous phase or the addition of small quantities of water to the reaction mixture (c.f. EP O 583 712 A2) in order to increase the durability and thus the service life of the catalyst.

Organofunctional polysiloxane catalysts need not be pretreated in phenol for bisphenol A synthesis.

They exhibit very high mechanical and hydrodynamic stability; thus, even at elevated throughputs (increase of space/time yields c. f. DE 43 12 039 A1), the stated hydraulic problems do not occur.

The OFP catalysts exhibit higher catalytic reactivity per active center on the surface. In comparison with sulphonic acid organic ion exchangers, the OFP catalysts exhibit a higher reaction rate. This greater number of catalytic cycles in the OFP catalysts in particular results, even at elevated conversions of the carbonyl compounds used, in constantly uniform reactivities and in an improvement in yields of, for example, bisphenol A.

The following examples further illustrate specific embodiments of the invention.

Example 1

In a stirred apparatus, 10 g of an organofunctional polysiloxane produced and dried according to DE 195 36 363 of the composition stated below (specific surface area: 660 to 670 $m^2/g$; total pore volume: 2.50 to 2.60 ml/g; bulk density: 285 to 290 g/l; acid capacity 0.55 to 0.75 mmol $H^+/g$ of catalyst) are stirred with 70.58 g of phenol and 4.35 g of acetone at 70° C. until conversion of the acetone is complete. Bisphenol A yields are determined by gas chromatography.

| Composition of catalysts | Yield of p/p-bisphenol A | Selectivity for p/p-bisphenol |
|---|---|---|
| 36 $SiO_2 \cdot 4SiO_{3/2}(CH_2)$-$SO_3H \cdot SiO_{3/2}(CH_2)_3SH$ | 80% | 85.5 |
| 9 $SiO_2 \cdot SiO_{3/2}(CH_2)_3SO_3H \cdot SiO_{3/2}(CH_2)_3SH$ | 94% | 94.5% |
| 9 $SiO_2 \cdot SiO_{3/2}(CH_2)_3SO_3H \cdot 2 SiO_{3/2}(CH_2)_3SH$ | 95% | 95.0% |
| 9 $SiO_2 \cdot SiO_{3/2}(CH_2)_3SO_3H \cdot 3SiO_{3/2}(CH_2)_3SH$ | 96% | 95.5% |

Example 2

In a stirred apparatus, 20 g of an organofunctional polysiloxane produced and dried according to DE 195 36 363 of the composition 9 $SiO_2$ . $SiO_{3/2}(CH_2)_3SO_3H$ . 2 $SiO_{3/2}(CH_2)_3SH$ and having the physical characteristics stated in Example 1 are stirred with 141.16 g of phenol and 8.71 g of acetone at 100° C. The purity and quantity of products are determined by gas chromatography.

| Time in h | Acetone conversion | Yield of p/p-bisphenol A | Selectivity for p-p-bisphenol A |
|---|---|---|---|
| 0.5 | 60% | 57% | 94% |
| 2 | 89% | 87% | 94% |
| 4 | 99% | 97% | 95% |

Example 3

A cylindrical reactor (diameter 28 mm×length 170 mm) is filled with 30 g (92 ml) of an organofunctional polysiloxane produced and dried according to DE 195 36 363 of the composition 9 SiO$_2$ . SiO$_{3/2}$(CH$_2$)$_3$SO$_3$H . 2 SiO$_{3/2}$(CH$_2$)$_3$SH and having the physical characteristics stated in Example 1. 3.3 g/min of a phenol/acetone mixture in a 10:1 molar ratio are passed through the catalyst. The calculated WHSV value is 6.7/h. The temperature in the fixed bed is 75° C. Using gas chromatography, acetone conversion is determined at 41.9% and selectivity for the para/para isomer of bisphenol A at 91.1%. The sulphur content in the product stream is below 0.01 mg/g of solution (less than 10 ppm).

Comparative Example 3

In a cylindrical reactor (diameter 28 mm×length 170 mm), 3.3 ml/min of a phenol/acetone melt in a 10:1 molar ratio are passed through 35 g of pretreated phenol-moistened, Lewatit SP 120 organic ion exchange resin (H$^+$ form) modified according to DE-A 36 19 450 or DE-A 37 27 641 with 25 mol. % of 2-mercaptoethylamine at an internal reactor temperature of 75° C. The WHSV value is 5.7/h. Acetone conversion is 12.5%, p/p-bisphenol A selectivity is 78%. The sulphur content in the product stream is determined at 0.061 mg/g of solution (about 61 ppm).

Example 4

80g/h of a phenol/acetone mixture in a 10:1 molar ratio are passed at a temperature of the fixed bed of 75° C. through a cylindrical reactor (45 mm×150 mm) filled with 60 g of an organofunctional polysiloxane produced and dried according to DE 195 36 363 of the composition 9 SiO$_2$ . SiO$_{3/2}$(CH$_2$)$_3$SO$_3$H . 2 SiO$_{3/2}$(CH$_2$)$_3$SH and having the physical characteristics stated in Example 1. The WHSV is 1.3/h. Acetone conversion is 81.0%, selectivity for para/parabisphenol A is 94.0%.

Example 5

50g/h of a phenol/acetone mixture in a 10:1 molar ratio are passed at a temperature of the fixed bed of 75° C. through a cylindrical reactor (45 mm×150 mm) filled with 60 g of an organofunctional polysiloxane produced and dried according to DE 195 36 363 of the composition 9 SiO$_2$ . SiO$_{3/2}$(CH$_2$)$_3$SO$_3$H . 2 SiO$_{3/2}$(CH$_2$)$_3$SH and having the physical characteristics stated in Example 1. The WHSV is 0.8/h. Using gas chromatography, acetone conversion is determined at 95.6%, selectivity for para/para-bisphenol A at 95.4%.

Example 6

60 g/h of a phenol/acetone mixture in a 10:1 molar ratio are passed at a temperature of the fixed bed of 75° C. through two cylindrical reactors (45 mm×150 mm) directly connected together in series and filled with a total of 120 g of an organofunctional polysiloxane produced and dried according to DE 195 36 363 of the composition 9 SiO$_2$ . SiO$_{3/2}$(CH$_2$)$_3$SO$_3$H . 2 SiO$_{3/2}$(CH$_2$)$_3$SH. The WHSV is 0.5/h. Acetone conversion is 98.2%, selectivity for the para/para-bisphenol A isomer is 95.5% and selectivity for the total quantity of bisphenol A (sum of p/p and o/p product) is 99.95%.

Summary of results in the continuously operated fixed bed reactor. Examples 3 to 6

| WHSV in h$^{-1}$ | Acetone conversion | Yield of p/O-BPA | Selectivity for p/p-BPA | Selectivity for p/p-BPA and o/p-BPA |
|---|---|---|---|---|
| 0.5 | 98.2% | 95.9% | 95.5% | 99.95% |
| 0.8 | 95.6% | 92.5% | 95.4% | 99.31% |
| 1.3 | 81.0% | 76.2% | 94.0% | 99.02% |
| 6.7% | 41.9% | 38.5% | 91.1% | 94.11% |

Further variations and modification of the foregoing will be apparent to those skilled in the art and are intended to be encompassed by the claims appended hereto.

German priority application 195 36366.3 is relied on and incorporated herein by reference.

We claim:

1. A process for the production of a 2.2'-bis(4-hydroxyphenyl)propane comprising reacting together the corresponding phenol and carbonyl compound at a temperature of between 40° and 150° C. and in the presence of a shaped organopolysiloxane containing sulphonate and mercapto groups as the catalyst, consisting of units of the formula $$[O_{3/2}-Si-R^1-SO_3-]_xM^{x+} \quad (I),$$

wherein R$^1$ is a linear or branched alkylene group having 1 to 12 C atoms, a cycloalkylene group having 5 to 8 C atoms or a unit of the general formulae

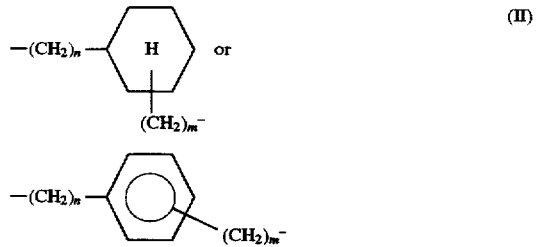

(II)

in which n or m is a number from 0 to 6 and states the number of methylene groups connected in the silicon or sulphur position, M equals H$^+$or optionally also NH$_4$+ or a metal ion having a valency of x equals 1 to 4, and units of the formula $$O_{3/2}-Si-R^2-SH \quad (III)$$

where R$^2$=R$^1$, wherein the free valencies of the oxygen atoms attached to the silicon atoms are saturated by the silicon atoms of further groups of the formulae (I) and/or (II) and/or by the groups of the crosslinking linking members of the formulae SiO$_{4/2}$  (IV)

optionally R"SiO$_{3/2}$, R'SiO$_{3/2}$, R'$_2$SiO$_{2/2}$ and optionally AlO$_{3/2}$, R'AlO$_{2/2}$ and/or TiO$_{4/2}$, R'TiO$_{3/2}$, R'$_2$TiO$_{2/2}$  (V)

wherein R' is a methyl or ethyl group, R" means phenyl or a linear or branched C$_2$—C$_{12}$ alkyl group and the ratio of groups of the formula (I) to groups of the formula (III) ranges from 10:1 to 1:10, the ratio of groups of the formula (I) to groups of the formula SiO$_{4/2}$ ranges from 1:3 to 1:20 and the ratio of groups of the formula SiO$_{4/2}$ to groups of the formula (V) ranges from 1:0 to 1:0.5.

2. The process according to claim 1 wherein, the desired product is separated.

3. The process according to claim 1, further comprising continuously passing a mixture of phenols according to the formula (IX) and carbonyl compounds according to the formula (X) in a molar ratio of 3:1 to 25:1 through a fixed bed reactor, and wherein formula IX is

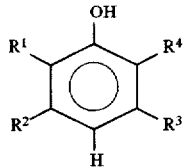

in which $R^1$, $R^2$, $R^3$ and $R^4$ mutually independently denote hydrogen, $C_1$ to $C_4$ alkyl, phenolic, $C_1$ to $C_4$ alkyl phenolic, phenyl phenolic or halogen substituted phenolic groups and wherein formula X is

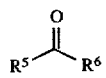

in which $R^5$ and $R^6$ mutually independently mean hydrogen, $C_1$ to $C_6$ alkyl, $C_6$ to $C_{10}$ cycloalkyl, $C_6$ to $C_{14}$ aryl $C_7$ to $C_{20}$ araalkyl, $C_7$ to $C_{20}$ alkylaryl or $R^5$ to $R^6$ form a saturated ring having 5 to 6 carbon atoms.

4. The process according to claim 3, wherein said mixture is passed through the fixed bed reactor at a WHSV of 0.25 to 24 $h^{-1}$.

5. The process according to claim 1, wherein the ratio of SH groups to $SO_3H$ groups on the catalyst is between 1:10 and 10:1.

* * * * *